United States Patent [19]

Balding et al.

[11] Patent Number: 4,829,448
[45] Date of Patent: May 9, 1989

[54] AIR-IN-LINE DETECTOR

[75] Inventors: Alan S. Balding; Nigel F. Carter, both of Oxfordshire; Paul F. Frampton, Surrey; Vincent A. Rosso, Oxfordshire, all of Great Britain

[73] Assignee: Vi-tal Hospital Products Ltd., Reading, England

[21] Appl. No.: 777,202

[22] Filed: Sep. 18, 1985

[30] Foreign Application Priority Data

Sep. 24, 1984 [GB] United Kingdom ................. 8424101

[51] Int. Cl.$^4$ .......................... A61M 5/16; G08B 21/00
[52] U.S. Cl. ................................ 364/509; 364/413.02; 128/DIG. 13; 128/633; 73/861.41; 340/609; 340/619
[58] Field of Search ............... 364/413, 415, 416, 507, 364/509, 510; 340/606, 609, 619, 632; 73/861.04, 861.41; 128/DIG. 13, 766, 632, 633

[56] References Cited

U.S. PATENT DOCUMENTS

| | | | |
|---|---|---|---|
| 4,114,144 | 9/1978 | Hyman | 128/DIG. 13 |
| 4,367,736 | 1/1983 | Gupton | 128/DIG. 13 |
| 4,370,983 | 2/1983 | Lichtenstein | 128/630 |
| 4,469,480 | 9/1984 | Figler et al. | 128/DIG. 13 |
| 4,509,943 | 4/1985 | Hanzawa | 128/DIG. 13 |
| 4,565,500 | 1/1986 | Jeensalute et al. | 128/DIG. 13 |
| 4,658,244 | 4/1987 | Meijer | 128/DIG. 13 |

*Primary Examiner*—Parshotam S. Lall
*Assistant Examiner*—Brian M. Mattson
*Attorney, Agent, or Firm*—Jeffers, Hoffman, Niewyk

[57] ABSTRACT

An air-in-line detector for detecting the presence of air in a translucent tube (8) containing a liquid comprises a channel (18) for receiving the tube, only three radiation emitter detector pairs (11, 12; 13, 14; 15, 16) two of which (11, 12; 15, 16) are arranged to detect the presence of an opaque liquid with the emitter (11, 15) and detector (12, 16) of each pair being located on opposite sides of the channel (18) so that radiation emitted by the radiation emitters impinges directly on their associated detectors and one (13, 14) of which is arranged to detect the presence of translucent liquids with its emitter (13) and detector (14) being located on opposite sides of the channel (18) but not directly aligned so that radiation emitted by the radiation emitter (13) only impinges on its associated detector (14) after refraction by the tube (8) filled with a translucent liquid, and a programmed computer (1). The computer (1) is coupled to the emitters and detectors and is programmed to monitor their outputs and to give an indication indicating the presence of air in the tube (8) except when the outputs of all three detectors (12, 14, 16) show that none of them are receiving radiation from the associated emitters (11, 13, 15) or that all of them (12, 14, 16) are receiving radiation from their emitters (11, 13, 15) but no longer continue to do so when the emitter (13) of the translucent liquid emitter-detector pair (13, 14) is turned off.

28 Claims, 4 Drawing Sheets

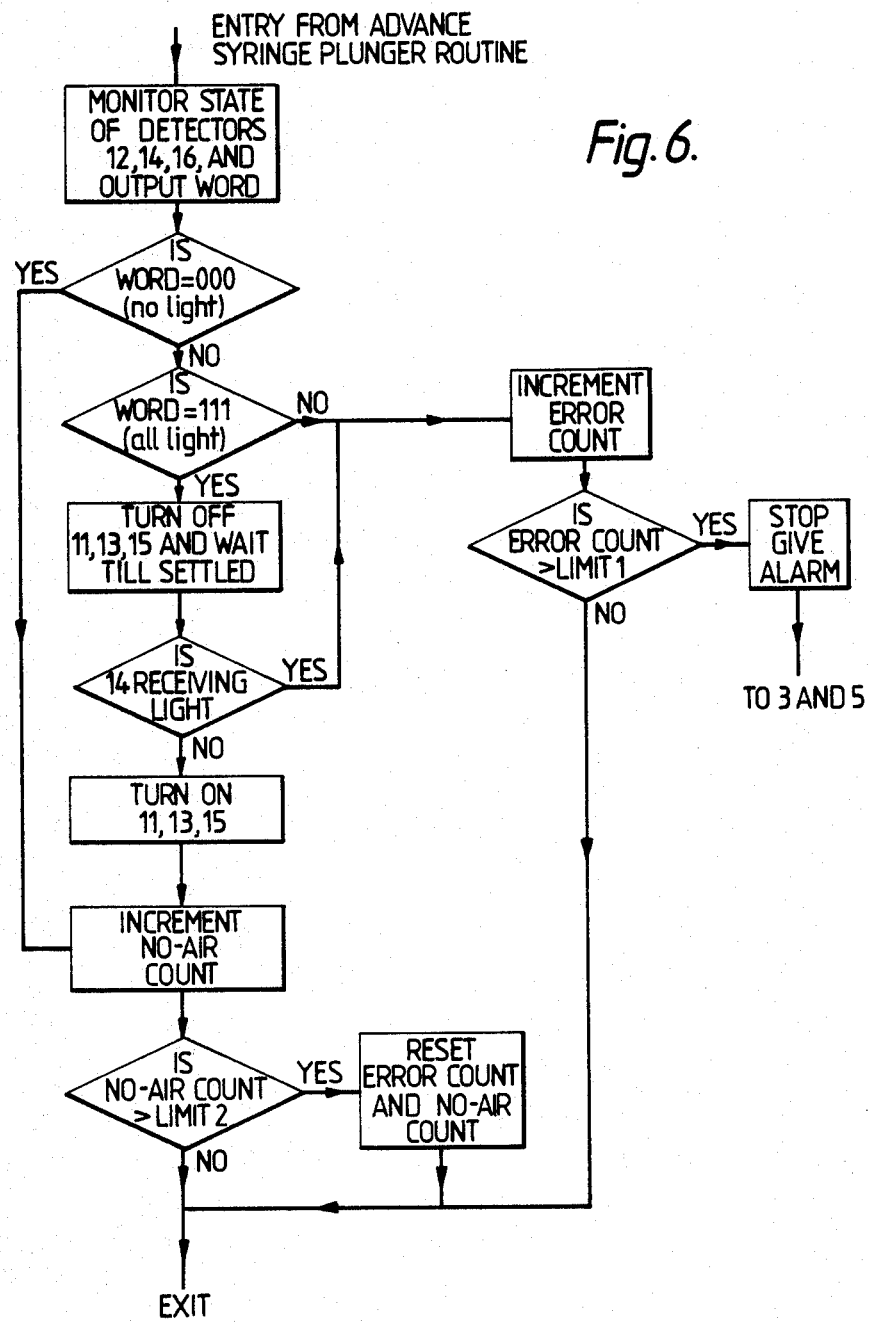

AIR-IN-LINE DETECTOR

FIELD OF THE INVENTION

This invention relates to an air-in-line detector for detecting the presence of air bubbles in a tube carrying a liquid. The present invention has particular application with medical liquids such as translucent or transparent medical liquids, for example intravenous drug solution, food solution or other bodily liquids including blood which is infused into a patient. In all of these cases, it is important that the minimum amount of air is infused into a patient. Air bubbles of substantial size are extremely dangerous if they are infused into a patient and can result in the patient's death.

BACKGROUND OF THE INVENTION

To avoid this problem, various proposals have been made previously to provide air-in-line detectors so that the presence of any air bubbles in a liquid line leading to a patient can be detected and an alarm raised. Air-in-line detectors have to detect the presence of air in both opaque liquids such as blood and transparent or translucent liquids, and consequently, such detectors are relatively complicated. It is also very desirable for the detectors to be fail-safe so that an alarm condition is raised when any single component within the device fails to ensure that the patient is safeguarded to the maximum extent. One of the results of such existing systems is that repeated false alarms occur, and this is dangerous because repeated false alarms can result in a correct alarm signal being ignored.

One example of an air-in-line detector for detecting the presence of air in a translucent tube containing liquid is described in GB-A-1550060. This specification describes a fluid detector comprising a channel for receiving the tube and five radiation emitter-detector pairs; three of which are arranged to detect the presence of an opaque liquid with the emitter and detector of each pair being located on opposite sides of the channel so that radiation emitted by the radiation emitters impinges directly on their associated detectors and two of which are arranged to detect the presence of translucent liquids with the emitter and detector of each pair being located on opposite sides of the channel but not directly aligned so that radiation emitted by the radiation emitters only impinges on its associated detector after refraction by the tube filled with a translucent liquid.

This existing device also includes a logic circuit which analyzes the outputs of the detectors and provides an alarm when air is detected in the transparent tube. The logic circuit includes a steering gate coupled to the top detector and depending upon whether the top detector receives a light or dark response this preconditions the remainder of the logic circuit to look for air in an opaque liquid or look for air in a transparent liquid. The other detectors are used as two separate pairs each pair of which detects air in the line by looking for an air bubble of sufficient size to be present in the path of both detectors of that pair.

The detector described thus automatically takes account of whether the liquid in the tube is opaque or translucent and can take account of some single component failures. However, for example, if the lowest radiation emitter ceases to emit radiation, or the radiation path between this and its associated detector is blocked by debris or, for example, the detector fails and is permanently open circuit, the logic circuit fails to detect any problem. Further, if such a faulty system is used with an opaque liquid, the top radiation emitter-detector pair preconditions the logic circuit to look for coincidence of signals from one or other of the two lower radiation detector radiation emitter pairs to indicate the presence of an air bubble large enough to bridge the detectors in one of the pairs.

What should happen now is that an alarm should be raised, but the faults described above would prevent the bottom detector even giving a signal, and thus, the required coincidence never occurs and consequently unlimited amounts of air could be infused into a patient without an alarm signal being given. This is not the only single component failure which could be life threatening in the arrangement shown and described in this patent specification.

This conventional air-in-line detector also, erroneously gives an alarm indication if a transparent liquid replaces an opaque liquid in the tube and, vice versa since the logic circuit interprets the interface between the two liquids as the presence of an air bubble. A further limitation of this existing device is that it can only detect the presence of an air bubble of a particular size, namely of a size sufficient to bridge two successive radiation-detector emitter pairs and this is determined by the physical construction of the device. Clearly, it would be possible to have a number of substantially sized, but spaced, air bubbles in the tube and, under these circumstances such a string of bubbles would probably not initiate an alarm and yet their cumulative volume would be sufficient to be life threatening.

SUMMARY OF THE INVENTION

According to this invention, an air-in-line detector for detecting the presence of air in a translucent tube containing a liquid comprises a channel for receiving the tube, only three radiation emitter detector pairs, two of which are arranged to detect the presence of an opaque liquid with the emitter and detector of each pair being located on opposite sides of the channel so that radiation emitted by the radiation emitters impinges directly on their associated detectors and one of which is arranged to detect the presence of translucent liquids with its emitter and detectors being located on opposite sides of the channel but not directly aligned so that radiation emitted by the radiation emitter only impinges on its associated detector after refraction by the tube filled with a translucent liquid; and a programmed computer coupled to the emitters and detectors programmed to monitor the outputs of the detectors and programmed to give an alarm indication indicating the presence of air in the tube except when the outputs of all three detectors show that none of them are receiving radiation from their associated emitters or that all three are receiving radiation from their emitters but no longer continue to do so when the emitter of the transparent liquid detecting the emitter-detector pair is turned off.

The air-in-line detector in accordance with this invention is firstly less complex than the conventional device and, since it uses less components, it tends to have a greater reliability. In addition to this, failure of any single component is detected by the programmed computer and consequently the existence of each and every single component failure initiates an alarm.

Preferably, the programmed computer is also programmed to carry out an initial start-up routine to check the operation and function of both of the opaque liquid emitter and detector pairs before the tube is introduced into the channel. In this start-up routine, the outputs of both detectors are monitored both before, and after, their corresponding emitters are switched on. This provides a check that both the detector and the emitter of each pair is operating satisfactorily. After this initial start-up check the subsequent, simultaneous failure of both the opaque emitter-detector pairs is very unlikely the subsequent checks performed by the computer to detect the failure of any one of these devices.

With the air-in-line detector in accordance with this invention, the presence of even small air bubbles can be detected since the presence of any air in the tube interferes with the beam of radiation passing between a single radiation emitter-detector pair and influences the operation of the device. Accordingly, it is preferred that the detector also includes an error counter which is incremented by the programmed computer each time the presence of air in the radiation paths of one of the emitter-detector pairs is detected. This error counter is then incremented on each occasion that air is present but only triggers the alarm when a predetermined count has been reached in the error counter. This ensures that spurious false alarm signals are not given by the presence of only very small air bubbles and also enables the detector to take account of a string of small air bubbles the cumulative volume of which may be sufficient to provide a threat to a patient.

Preferably, the detector also includes a no-air counter which is incremented each time the tube is monitored and no air is detected in the radiation paths of any of the detectors. Preferably, the output of this no-air counter is used to re-set the error counter and normally the setting of the no-air counter to cause resetting of the error counter is many times greater than the count that has to be accumulated in the error counter before an alarm signal is given. As an example, the count that is accumulated in the no-air counter before it resets the error counter may be between ten and fifty times greater than the count in the error counter which triggers the alarm to ensure that the error counter is only re-set after a considerable quantity of air-free liquid has been infused into the patient.

Preferably, the air-in-line detector in accordance with this invention is associated with a fluid delivery mechanism, for example a syringe driver or volumetric infusion pump, and, under these circumstances, the air-in-line detector monitors the tube before each actuation of the syringe driver or infusion pump. The air-in-line detector may also be arranged to disable the fluid delivery mechanism and thereby prevent its actuation when the alarm is triggered.

BRIEF DESCRIPTION OF THE DRAWINGS

A particular example of a syringe driver including an air-in-line detector in accordance with this invention will now be described with the accompanying drawings, in which.

DESCRIPTION OF PREFERRED EXAMPLE

Figure 1:
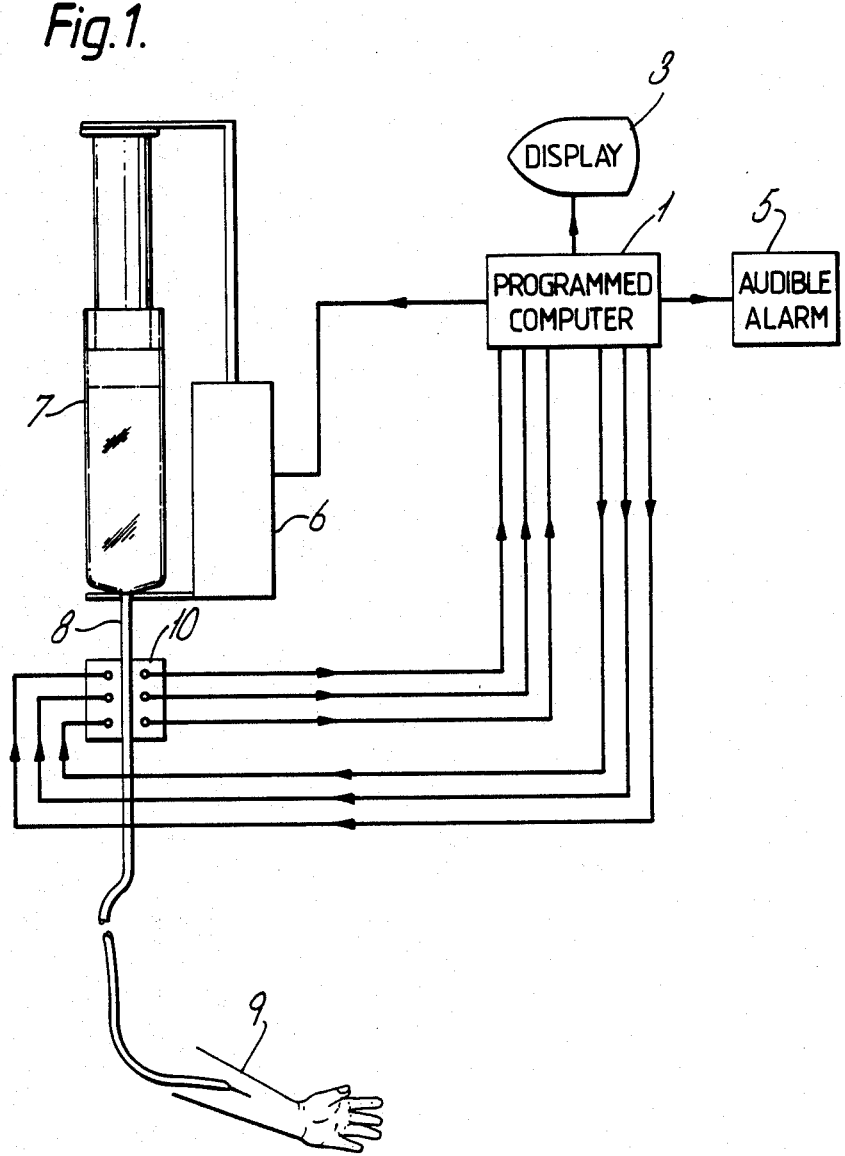
FIG. 1 is a diagram of the syringe driver.

This example of a syringe driver includes a programmed computer 1 such as model no. 6301 manufactured by Hitachi, a message display 3 such as a liquid crystal display or array of light emitting diodes, an audible alarm 5, and a syringe piston actuator 6 acting on the piston of a syringe 7. An infusion tubing set 8 is connected to the syringe 7 and, in use, leads to a cannulla inserted in a vein in a patient's arm 9. The infusion tubing set 8 is inserted in a monitoring head 10 of the syringe driver.

Figure 3:
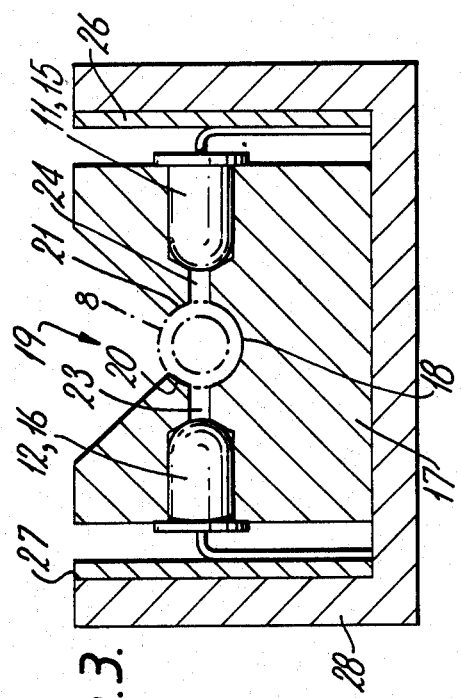
FIG. 3 is a section taken along the line A—A and C—C of FIG. 2.
Figure 4:
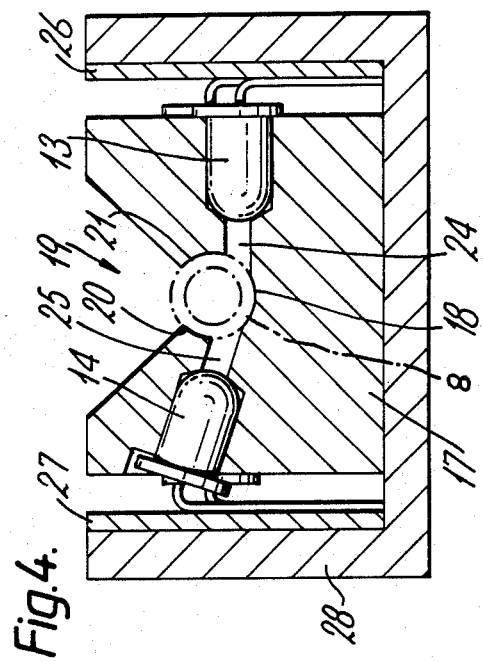
FIG. 4 is a section taken along the line B—B of FIG. 2.
Figure 2:
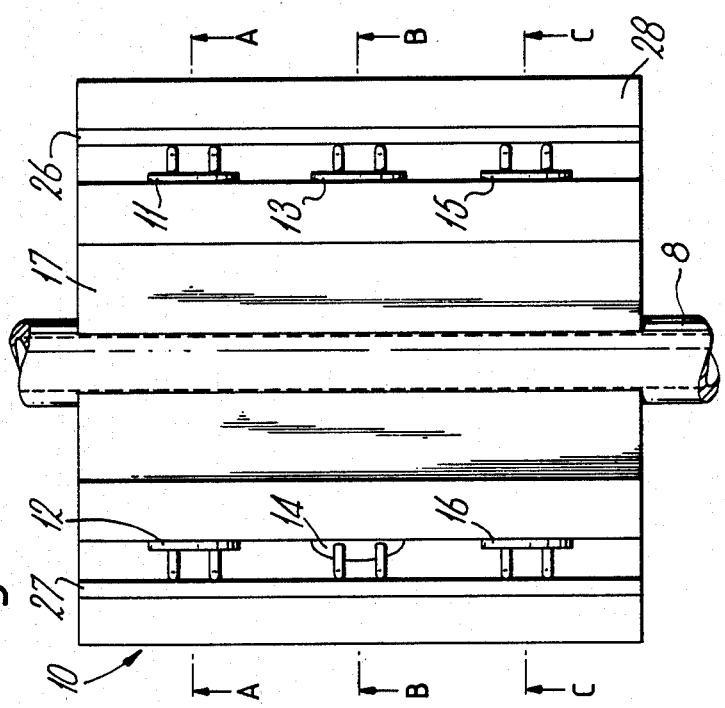
FIG. 2 is a plan of a monitoring head of the device.

The monitoring head 10 includes three infrared photoemitter, photodetector pairs 11 and 12, 13 and 14 and 15 and 16, respectively. The monitoring head 10 includes a block 17 containing a channel 18 with a diverging entry portion 19 and inwardly facing ribs 20 and 21 beneath which the standard transparent and flexible infusion tubing set 8 can be snap fitted. The photodetector and photoemitter pairs 11 and 12, 13 and 14, and 15 and 16 are mounted in bores in the sides of the block 17 and communicate with one another by passageways passing through the groove 18 and, in use, through the tubing 8 and its contents. The emitters 11 and 15 and detectors 12 and 16 are arranged at ends of passageways 23 and 24 which extend diametrically across the tubing 8 as shown in FIG. 2. The emitter 13 and detector 14 are arranged so that passageways 24 and 25 provide the path of radiation from the emitter 13 to the detector 14 and these passageways are not directly aligned and are almost tangential to the tubing 8 as shown in FIG. 3. The emitters and photodetectors are connected to circuit boards 26 and 27 respectively. The entire syringe driver is mounted within a single housing.

The operation of each of the emitters 11, 13 and 15 is under the control of the programmed computer 1 and the outputs from the detectors 12, 14 and 16 are also fed to the programmed computer 1. The programmed computer also drives the display 3 and the audible alarm 5 and drives the piston actuator 6 to drive liquid through the tubing 8 and into the patient. Preferably, the display 3 also gives alarm information and is also used to provide other information to the user.

Figure 5:
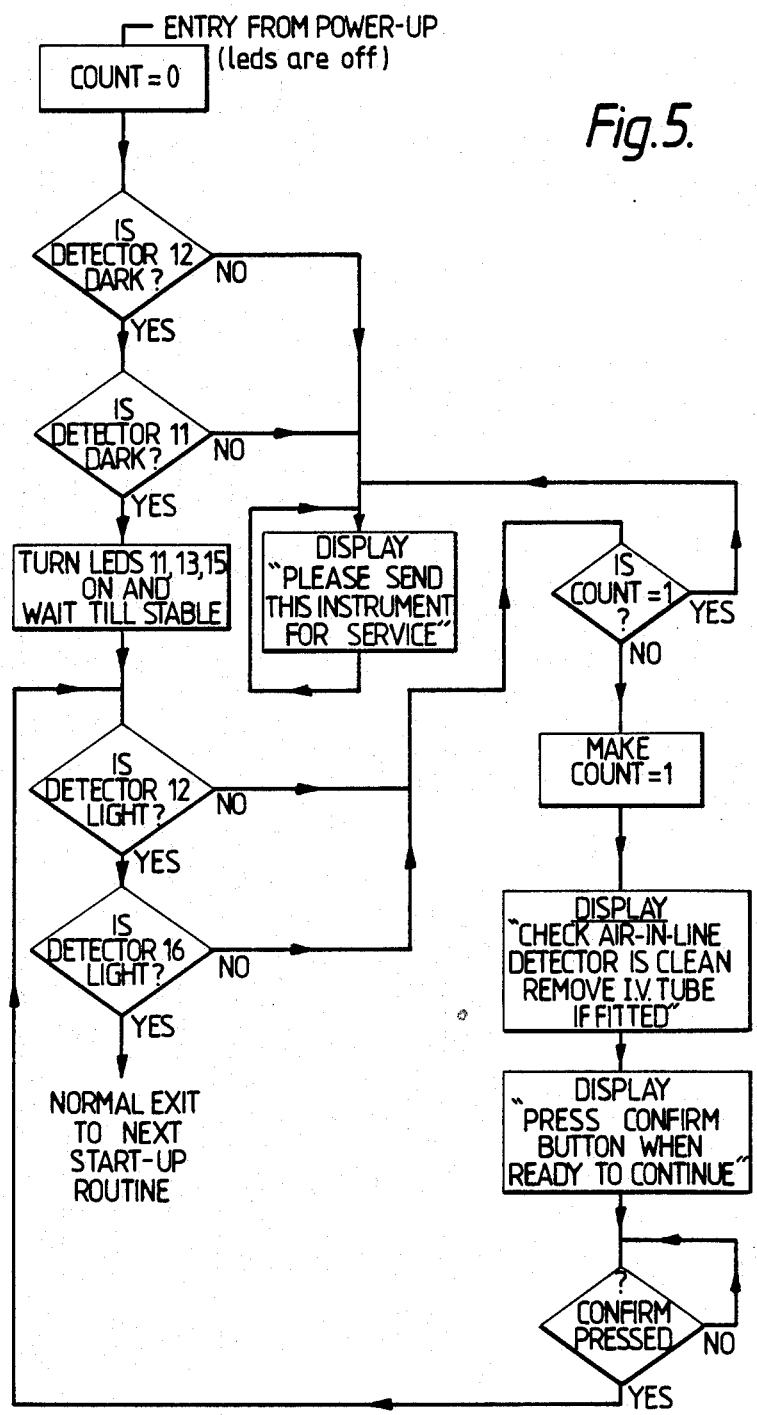
FIG. 5 is a flow diagram of a start-up routine; and,
FIG. 6 is a flow diagram of the air detection routine.

Initially, the detector is powered-up without the tubing 8 being present in the channel 18. When the device is powered-up the computer 1 performs the check illustrated in the flow diagram shown in FIG. 5. Thus, the computer initially checks that the detector 12 is giving a dark response that is the detector 12 is not receiving any light. If it is found that detector 12 is giving an output, an indication is given on the display 3 which reads "Please send this instrument for service". If a dark response is obtained from the detector 12 then the same check is carried out on detector 16. Again if a light response is obtained the indication is given that the equipment needs servicing but if a dark response is obtained then the computer 1 switches on the light emitting diodes 11, 13 and 15 and instigates a short delay until the instrument is stabilized. Outputs from the detectors 12 and 16 are then checked once again and if both give an indication of the presence of light at this time then the start-up routine is recorded as having been completed normally.

If the photodetector 12 does not receive any light, then an indication is given in the display 3 which reads "Check air-in-line detector is clean, remove I.V. tube if fitted". Clearly, a nil response is obtained if tubing with an opaque fluid is already present in the monitoring head 10 and this gives the operator an opportunity to remove the tubing if, it has previously inadvertently, been fitted and an opportunity to clean the detectors and emitters to remove any deposits that were interfering with the beams of radiation. After a period of time, the display 3 then changes to read "Press confirm button when ready to contine". There is a simple push button switch on the side of the detector unit which can be pressed once the tube has been removed and/or once any accumulated deposits have been cleaned away. When the confirmation button has been pressed, the computer 1 repeats the check on the outputs of detectors 12 and 16 with their associated emitters emitting light and if outputs are still not obtained from both of these detectors the display 3 again reads "Please send this instrument for service". However, if both now provide a satisfactory output the start-up routine is again recorded as having been completed satisfactorily.

The computer 1 then controls the display 3 to give an indication that the tubing 8 should be fitted in the monitoring head 10, and the remainder of the equipment is set up and purged to provide an infusion into a patient. When the equipment has been set up satisfactorily the device is actuated to start infusing liquid into a patient. After the start signal has been provided by an operator, the computer 1 checks that air is not present in the tubing 8 before each and every actuation of the syringe piston actuator 6. The flow diagram of the program that is performed is shown in FIG. 6.

The computer is programmed to acquire the outputs of the detectors 12, 14, 16 and form a three bit data word with each bit corresponding to the state of its respective detector. The computer 1 is then programmed to examine the data word. If the word is 000 corresponding to each of the detectors 12, 14, 16 receiving no light, it shows that an opaque liquid is contained in the tubing 8 and that no air is present. This causes a no-air counter formed by part of the computer 1 to be incremented by one count and initiates movement of the syringe piston actuator 6. If the word is 111 corresponding to all of the detectors 12, 14, 16 receiving light, it shows that a transparent or translucent liquid is present in the tubing 8 or that air is present in the tubing 8 and that the detector 14 has failed and is permanently providing a 1 output. To eliminate this possible source of error, the computer 1 then turns off the light emitting diodes 11, 13 and 15 and again waits for a short time until the outputs of the detectors have settled down. It then, once again, checks the output of detector 14. If it still gives a light response, the detector 14 must be faulty and accordingly an error counter formed by part of the computer 1 is incremented by one count. However, if a dark response is obtained from the output of detector 14, then the detector 14 is functioning correctly, and consequently, there must be a transparent liquid present in the tubing 8. The computer then turns on the light emitting diodes 11, 13 and 15 and again increments the no-air counter and initiates the movement of the syringe piston actuator 6.

If the data word has any other form, this shows that there is some form of fault, either the presence of some debris in a clear liquid obscuring the light path between one of the pairs or, the presence of an air bubble in one of the light paths with an opaque liquid. Thus, if the outputs from the detectors 12, 14 and 16 are unequal the error counter is incremented by one count.

Each time any sort of error or malfunction is detected, the error counter is incremented and this error counter is programmed with a particular limit. It may, for exmaple, be 512 steps of the syringe piston actuator 6 which, in practice only represents a small volume of, for example, one milliliter. The limit may be varied to give the degree of control required for particular situations. Once the number of error counts detected exceeds this count then the display 3 gives a message reading "Air in line", and the audible alarm 5 is triggered. The syringe piston actuator 6 is also disabled to stop further infusion into the patient.

If the count in the error counter is less than the programmed limit or no error has been detected, then the program continues allowing the syringe piston actuator 6 to carry out the infusion step and then waits until the next infusion step is required before the routine is repeated. When the no-air counter reaches the limit set in it, which typically is between ten and fifty times the limit set in the error counter, this shows that a considerable volume of liquid has passed through the tubing 8 without the error count in the error counter exceeding its limit, and accordingly, once the limit in the no-air counter has been achieved, both the error counter and the no-air counter are re-set to zero.

We claim:

1. An air-in-line detector for detecting presence of air in a translucent infusion tube containing a liquid comprising:
   a channel for receiving said tube;
   only three radiation emitter-detector pairs, two of said radiation emitter-detector pairs are opaque liquid emitter-detector pairs being arranged to detect presence of an opaque liquid with said emitter and said detector of each said pair being located on opposite sides of said channel whereby radiation emitted by said radiation emitters impinges directly on their associated detectors in absence of an opaque liquid and no radiation emitted by said radiation emitters impinges directly on their associated detectors in the presence of an opaque liquid, and one of said radiation emitter-detector pairs being arranged to detect presence of a translucent liquid commonly infused into a patient with said emitter and said detector of said one pair being located on opposite sides of said channel with said detector and emitter not being directly aligned whereby radiation emitted by said radiation emitter only impinges on its associated detector after refraction by said tube filled with said translucent liquid; and,
   a programmed computer means coupled to said emitters and said detectors, programmed to monitor said detectors and programmed to give an indication indicating presence of air in said tube except when one of the following conditions is satisfied:
   (a) outputs of all three said detectors show that none of them are receiving radiation from their associated emitters; and,
   (b) outputs of all three said detectors show that all are receiving radiation from their emitters and no longer continue to do so when said emitter of said pair to detect the presence of a translucent liquid is turned off.

2. The air-in-line detector of claim 1, wherein said programmed computer means is also programmed to carry out an initial start-up routine, said start-up routine checking operation and function of both of said opaque liquid emitter and detector pairs before said tube is introduced into said channel by monitoring outputs of both detectors before, and after, their corresponding emitters are energised.

3. The air-in-line detector of claim 1 which also includes error counter means, said error counter means being incremented by said programmed computer means each time an indication is given of the presence of air and providing an alarm indication when it is incremented to a predetermined value.

4. The air-in-line detector of claim 3, in which also includes no-air counter means, said no-air counter means being incremented each time said tube is monitored and no indication is given of the presence of air, said no-air counter means providing an output to reset said error counter means when said no-air counter means is incremented to a predetermined value.

5. The air-in-line detector of claim 3, associated with a syringe driver, said syringe driver driving liquid through said tube, and wherein said air-in-line detector includes means for monitoring said tube before each actuation of said syringe driver.

6. The air-in-line detector of claim 5, wherein said computer means is programmed to disable said syringe driver and thereby prevent its actuation when said alarm indication is provided by said error counter means.

7. The air-in-line detector of claim 3, associated with a volumetric infusion pump, said volumetric infusion pump driving liquid through said tube and wherein said air-in-line detector includes means for monitoring said tube, before each actuation of said volumetric infusion pump.

8. The air-in-line detector of claim 7, wherein said computer means is programmed to disable said volumetric infusion pump and thereby prevent its actuation when said alarm indication is provided by said error counter means.

9. The air-in-line detector of claim 3, which also includes audible alarm means and wherein said programmed computer means is programmed to trigger said audible alarm means when an alarm indication is provided by said error counter means.

10. The air-in-line detector of claim 3, which also includes a message display device, and wherein said programmed computer means is programmed to provide a visual indication on said message display device when an alarm indication is provided by said error counter means.

11. The air-in-line detector of claim 10, wherein said programmed computer means causes said message display device to display messages identifying an event leading to an alarm indication being provided by said error counter means and to display instructions for an operation to be performed by an operator during loading and initiation of an infusion.

12. An air-in-line detector for detecting presence of air in a translucent infusion tube containing a liquid comprising:
 a channel for receiving said tube;
 three radiation emitter-detector pairs, two of said radiation emitter-detector pairs being arranged to detect presence of an opaque liquid which blocks transmission of radiation, and one of said radiation emitter-detector pairs being arranged to detect presence of a translucent liquid commonly infused into a patient;
 a programmed computer means coupled to said emitters and said detectors, programmed to monitor said detectors and programmed to give an indication indicating presence of air in said tube; and
 error counter means, said error counter means being incremented by said programmed computer means each time an indication of presence of air is given and providing an alarm indication when it has been incremented to a predetermined value.

13. The air-in-line detector of claim 12, in which also includes no-air counter means, said no-air counter means being incremented each time said tube is monitored and no indication is given of air in said tube, said no-air counter means providing an output to re-set said error counter means when said no-air counter means is incremented to a predetermined value.

14. The air-in-line detector of claim 13, associated with a syringe driver, said syringe driver driving liquid through said tube and wherein said air-in-line detector includes means for monitoring said tube before each actuation of said syringe driver.

15. The air-in-line detector of claim 14, wherein said computer means is programmed to disable said syringe driver and thereby prevent its actuation when said alarm indication is provided by said error counter means.

16. The air-in-line detector of claim 13, associated with a volumetric infusion pump, said volumetric infusion pump driving liquid through said tube and wherein said air-in-line detector includes means for monitoring said tube before each actuation of said volumetric infusion pump.

17. The air-in-line detector of claim 13, which also includes a message display device, and wherein said programmed computer means is programmed to provide a visual indication on said message display device when an alarm indication is provided by said error counter means.

18. An air-in-line detector for detecting presence of air in a translucent infusion tube containing a liquid comprising a channel for receiving said translucent tube, and three radiation emitter-detector pairs, two of said pairs are opaque liquid emitter-detector pairs being arranged to detect presence of an opaque liquid with said emitter and detector of each said pair being located on opposite sides of said channel whereby radiation emitted by the radiation emitters impinges directly on their associated detectors in absence of an opaque liquid and no radiation emitted by said radiation emitters impinges directly on their associated detectors in the presence of an opaque liquid and one of said pairs is a translucent liquid emitter-detector pair being arranged to detect presence of translucent liquids commonly infused into a patient with its emitter and detector being located on opposite sides of said channel but not directly aligned whereby radiation emitted by said radiation emitter only impinges on its associated detector after refraction by said tube filled with a translucent liquid, the improvement in which said detector includes only three radiation emitter-detector pairs, and includes a programmed computer means coupled to said emitters and said detectors, programmed to monitor outputs of said detectors and programmed to give an indication indicating presence of air in said tube except when one of the following conditions is satisfied:
 (a) said outputs of all three said detectors show that none of them are receiving radiation from their associated emitters; and
 (b) said outputs of all three said detectors show that said all three are receiving radiation from their emitters and no longer continue to do so when emitter of said translucent liquid emitter-detector pair is de-energized.

19. The air-in-line detector of claim 18, wherein said programmed computer means is also programmed to carry out an initial start-up routine, said start up-routine checking operation and function of both of said opaque liquid emitter and detector pairs before said tube is introduced into said channel by monitoring outputs of both said detectors before, and after, their corresponding emitters are energised.

20. The air-in-line detector of claim 18 including error counter means incremented by said programmed computer means each time presence of air is detected, said error counter means providing an alarm indication when a predetermined count is reached in said error counter means.

21. The air-in-line detector of claim 20, wherein said detector also includes no-air counter means which is incremented each time said tube is monitored and no air is detected, said no-air counter means providing an output to re-set said error counter means when said no-air counter means is incremented to a predetermined value.

22. The air-in-line detector of claim 20, associated with a syringe driver, said syringe driver driving liquid through said tube and wherein said air-in-line detector includes means for monitoring said tube before each actuation of said syringe driver.

23. The air-in-line detector according to claim 22, wherein said computer means is programmed to disable said syringe driver and thereby prevent its actuation when said alarm indication is provided by said error counter means.

24. The air-in-line detector of claim 20, associated with a volumetric infusion pump, said volumetric infusion pump driving liquid through said tube and wherein said air-in-line detector includes means for monitoring said tube before each actuation of said volumetric infusion pump.

25. The air-in-line detector according to claim 24, wherein said computer means is programmed to disable said volumetric infusion pump and thereby prevent its actuation when said alarm indication is provided by said error counter means.

26. The air-in-line detector according to claim 20, which also includes audible alarm means and wherein said programmed computer means is arranged to trigger said audible alarm means when an alarm indication is provided by said error counter means.

27. The air-in-line detector of claim 20, which also includes a message display device, and wherein said programmed computer means is programmed to provide a visual indication on said message display device when an alarm indication is provided by said error counter means.

28. The air-in-line detector of claim 27, wherein said programmed computer means causes said message display device to display messages identifying an event leading to an alarm indication being provided by said error counter means and to display instructions for an operation to be performed by an operator during loading and initiation of an infusion.

* * * * *